(12) United States Patent
Kilbey

(10) Patent No.: US 10,045,876 B2
(45) Date of Patent: Aug. 14, 2018

(54) WRIST ORTHOTIC INCLUDING ADJUSTABLE ULNA GAP

(71) Applicant: Bryan E. Kilbey, DeFuniak Sprs, FL (US)

(72) Inventor: Bryan E. Kilbey, DeFuniak Sprs, FL (US)

(*) Notice: Subject to any disclaimer, the term of this patent is extended or adjusted under 35 U.S.C. 154(b) by 729 days.

(21) Appl. No.: 13/886,350

(22) Filed: May 3, 2013

(65) Prior Publication Data

US 2014/0330188 A1    Nov. 6, 2014

(51) Int. Cl.
*A61F 5/00* (2006.01)
*A61F 5/058* (2006.01)
*A61F 5/01* (2006.01)

(52) U.S. Cl.
CPC ........ *A61F 5/05866* (2013.01); *A61F 5/0118* (2013.01)

(58) Field of Classification Search
CPC .. A61F 5/00; A61F 5/01; A61F 5/0102; A61F 5/0104; A61F 5/0118; A61F 5/013; A61F 13/00; A61F 13/04; A61F 13/10; A61F 13/107; A61F 13/108; A61F 5/05; A61F 5/058; A61F 5/05841; A61F 5/05858; A61F 5/05866
USPC ........ 128/846, 869, 878, 879; 602/5, 20, 21, 602/60–62, 64
See application file for complete search history.

(56) References Cited

U.S. PATENT DOCUMENTS

| | | | |
|---|---|---|---|
| 5,769,804 A * | 6/1998 | Harris et al. | 602/21 |
| 6,893,410 B1 * | 5/2005 | Hely | 602/21 |
| 7,056,298 B1 * | 6/2006 | Weber | A61F 5/0118 2/16 |
| 7,175,603 B2 * | 2/2007 | Fritsch et al. | 602/20 |
| 8,147,438 B2 * | 4/2012 | Livolsi | A61F 5/0118 602/20 |
| 2010/0298750 A1 * | 11/2010 | Chiang | A61F 5/0118 602/21 |

* cited by examiner

*Primary Examiner* — Kim M Lewis
(74) *Attorney, Agent, or Firm* — J. Wiley Horton

(57) ABSTRACT

An adjustable wrist orthotic suitable for the treatment of wrist fractures and similar injuries. The orthotic preferably includes a top panel joined to a bottom panel. The top and bottom panels are preferably joined by a radius connector which spans a "radius gap" between the top and bottom panel. An "ulna gap" may optionally be provided between the top and bottom panels as well. If an ulna gap is present, then an ulna connector is preferably provided to span this gap. A radius lace assembly is provided for adjusting the closure of the radius gap. The radius lace assembly is secured by placing a radius tab attached to a radius lace in a desired position on the exterior of the orthotic. Varying the placement position of the radius tab varies the taper of the radius gap so that the orthotic can accommodate wide variations in forearm geometry.

18 Claims, 12 Drawing Sheets

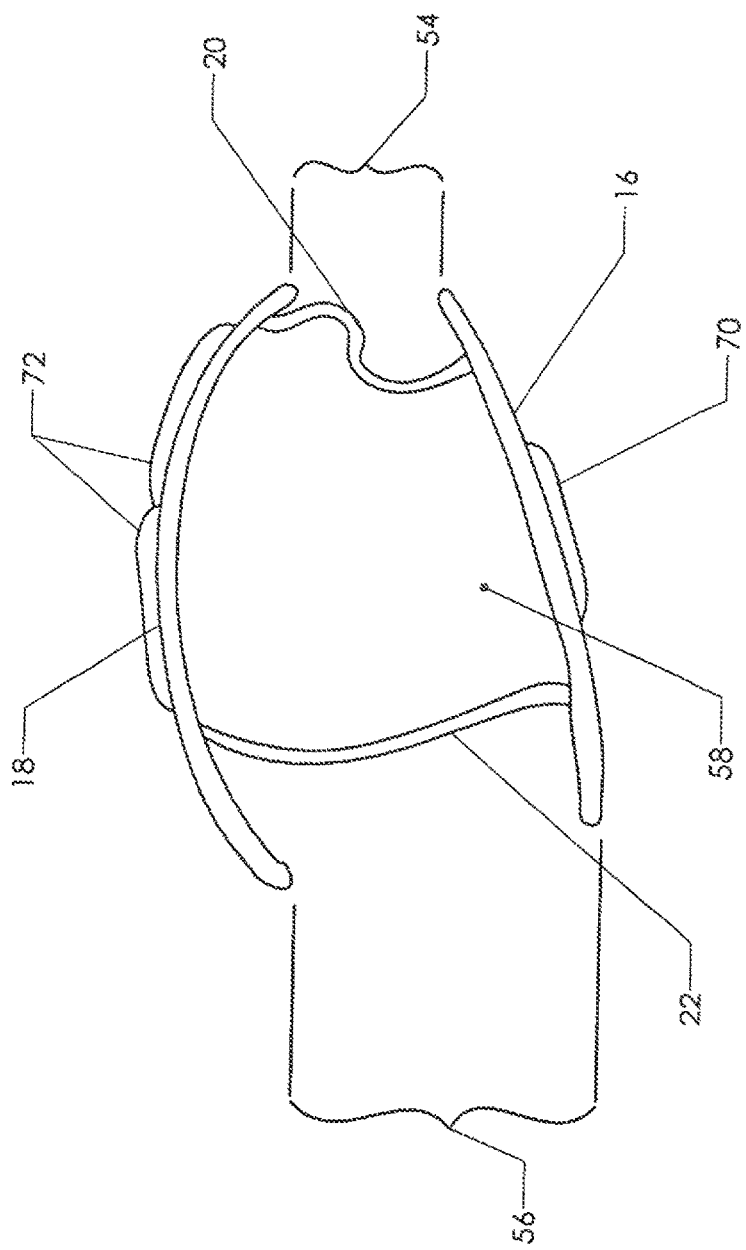

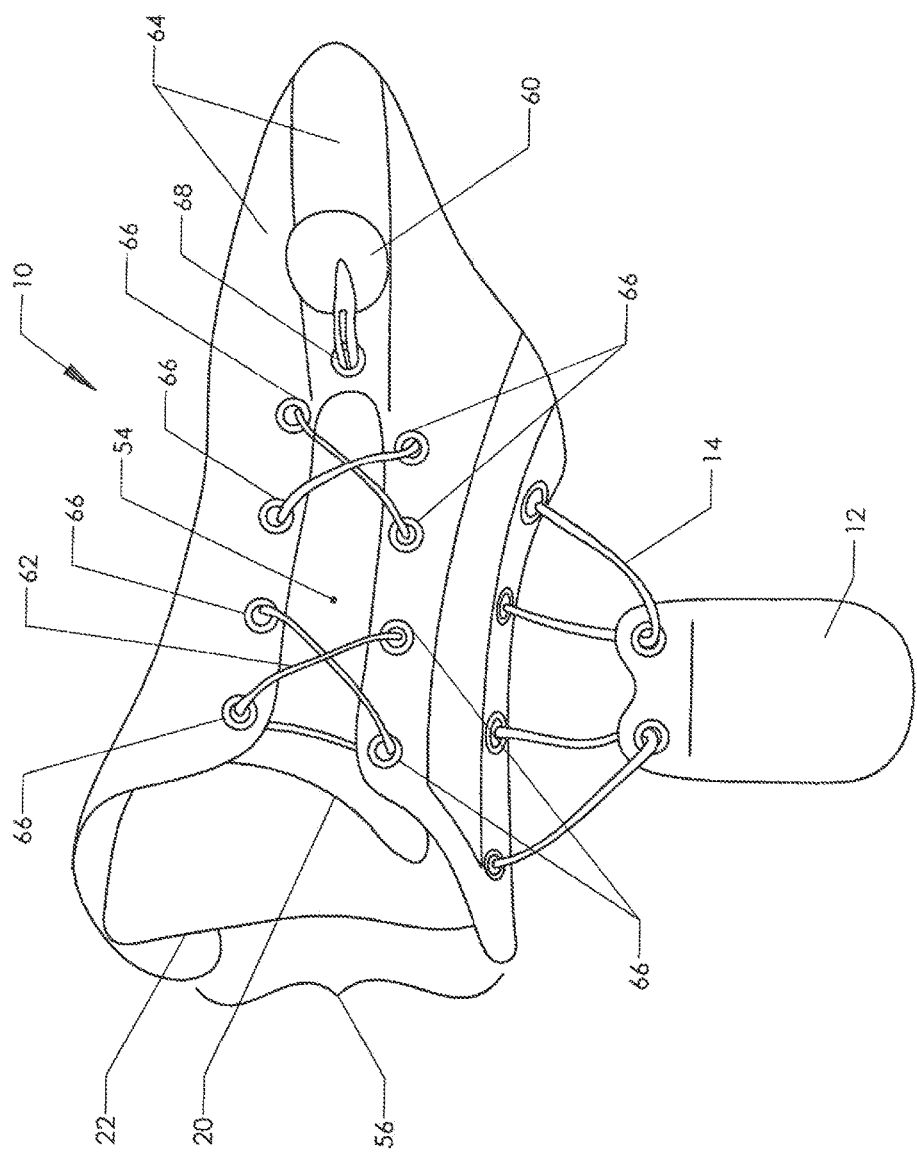

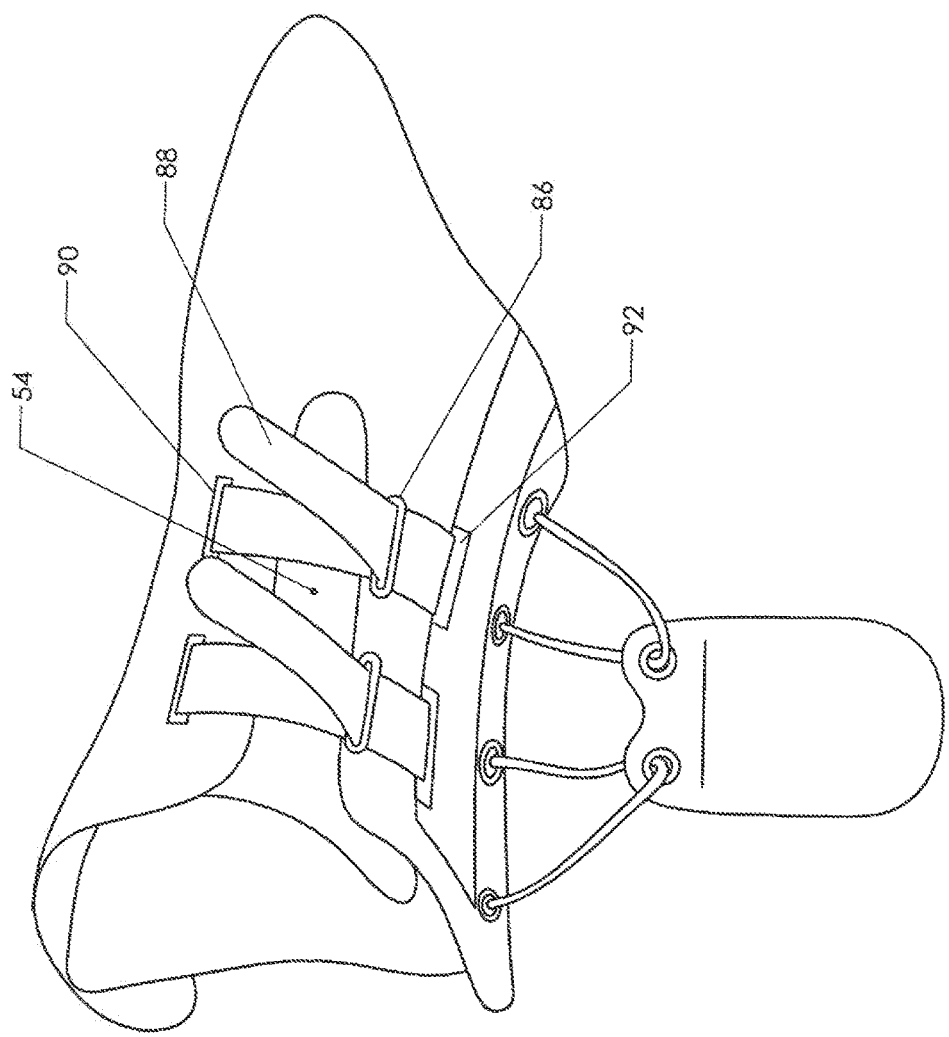

WRIST ORTHOTIC INCLUDING ADJUSTABLE ULNA GAP

CROSS-REFERENCES TO RELATED APPLICATIONS

This application is a non-provisional application claiming priority to U.S. Provisional Application No. 61/642,663 filed on May 4, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises a wrist orthotic which may be adjusted to accommodate a wide variety of anatomical differences.

2. Description of the Related Art

Wrist fractures were traditionally placed in plaster casts in order to immobilize the affected anatomy. In recent years, more flexible orthotic devices have replaced plaster casts. These usually encircle the wrist and palm with fabric material. One or more rigid stays are incorporated in the device in order to provide the requisite immobilization of the joint.

Elastic panels are used to adapt the orthotic to a range of sizes. Adjustable securing straps also aid proper fitting of the device. However, these adjustments have typically been limited to a relatively narrow range of sizes. Additionally, the geometry of the wrist and forearm varies widely from individual to individual. Some individuals have a moderate wrist diameter but very little expansion in the forearm when proceeding in the direction toward the elbow. Other individuals have similar wrist geometry but very rapidly expanding forearms.

The physician is thereby compelled to maintain a stock of orthotic devices in different sizes and geometries. Even with such a stock on hand, a patient with atypical wrist and forearm geometry may present for treatment. It would therefore be advantageous to provide a single wrist orthotic which could span a wide range of sizes and geometries. The present invention provides such a solution.

BRIEF SUMMARY OF THE PRESENT INVENTION

The present invention comprises an adjustable wrist orthotic suitable for the treatment of wrist fractures and similar injuries. The orthotic preferably includes a top panel joined to a bottom panel. The top and bottom panels are preferably joined by a radius connector which spans a "radius gap" between the top and bottom panel. A second "ulna gap" may optionally be provided between the top and bottom panels as well. If an ulna gap is present, then an ulna connector is preferably provided to span this gap. A thumb strap is preferably provided to secure a portion of the device over the palm.

A radius lace assembly is provided for adjusting the closure of the radius gap. A second adjustable closure mechanism—such as an ulna lace assembly—is preferably provided for adjusting the closure of the ulna gap when one is present. Both these adjustment features can be used to adjust the overall diameter of the brace. In addition, the radius lace assembly is secured by placing a radius tab attached to a radius lace in a desired position on the exterior of the orthotic. Varying the placement position of the radius tab varies both the width and the taper of the radius gap, so that the orthotic can accommodate wide variations in forearm geometry.

BRIEF DESCRIPTION OF THE SEVERAL VIEWS OF THE DRAWINGS

FIG. 1B is an elevation view, showing the attachment of the top and bottom panels using the radius and ulna connectors.

FIG. 2 is a perspective view, showing the ulna gap.

FIG. 11 is a perspective view, showing an alternate embodiment of the ulna gap closure mechanism.

REFERENCE NUMERALS IN THE DRAWINGS

| | | | |
|---|---|---|---|
| 10 | wrist splint | 12 | radius tab |
| 14 | radius lace | 16 | bottom panel |
| 18 | top panel | 20 | ulna connector |
| 22 | radius connector | 24 | bottom thumb relief |
| 26 | top thumb relief | 28 | thumb strap |
| 30 | tab | 31 | hook tab |
| 33 | first lace anchor | 34 | fourth eye |
| 36 | fifth eye | 38 | second lace anchor |
| 40 | first eye | 42 | third eye |
| 44 | sixth eye | 46 | eighth eye |
| 48 | second eye | 50 | seventh eye |
| 52 | hook panel | 54 | ulna gap |
| 56 | radius gap | 58 | central passage |
| 60 | ulna tab | 62 | ulna lace |
| 64 | loop covering | 66 | ulna eye |
| 68 | ulna tab eye | 70 | bottom stay pocket |
| 72 | top stay pocket | 74 | thumb |
| 75 | wrist | 76 | first finger |
| 78 | forearm | 80 | divergence angle |
| 82 | hand end | 84 | forearm end |
| 86 | strap ring | 88 | strap |
| 90 | strap anchor | 92 | strap ring anchor |

DETAILED DESCRIPTION OF THE INVENTION

The wrist splint of the present invention is preferably provided in separate right hand and left hand configurations. The two configurations are mirror images of each other. The following descriptions pertain to a right hand configuration.

Figure 1:
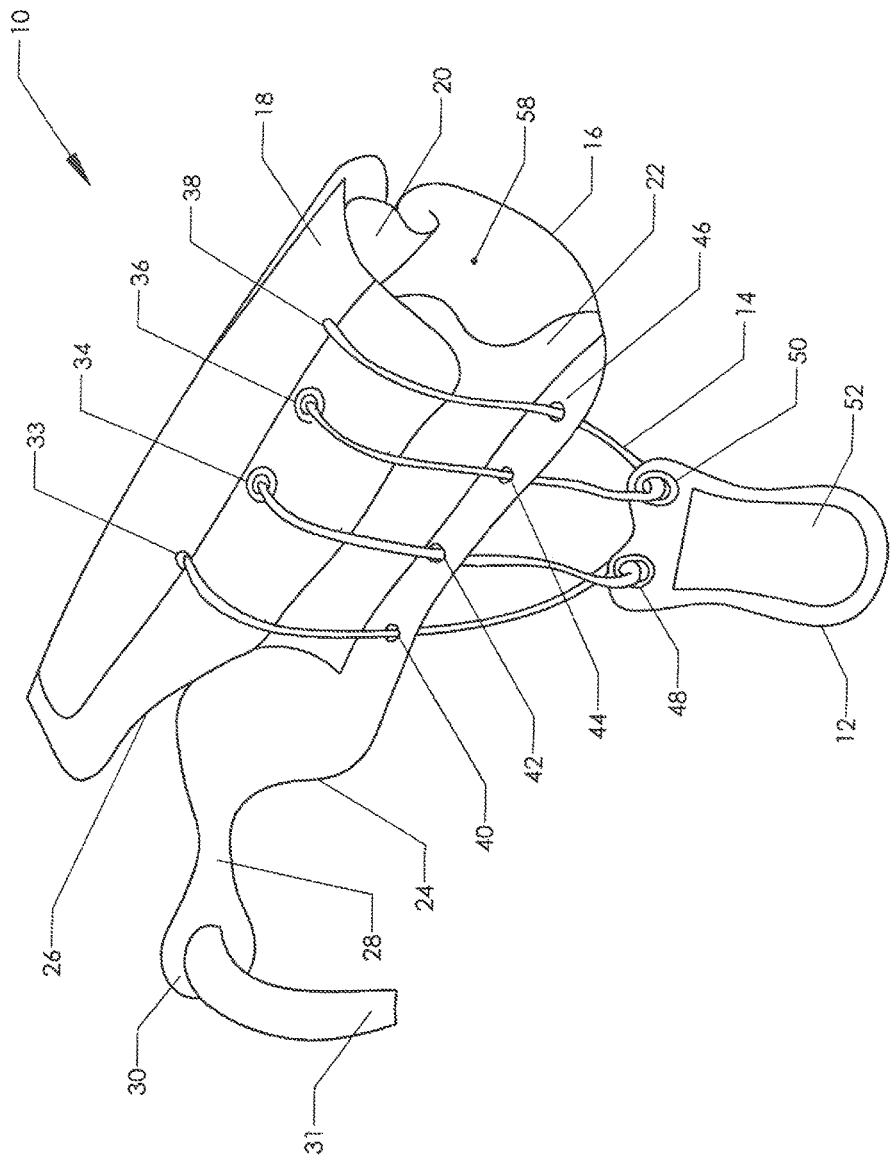
FIG. 1 is a perspective view, showing a wrist splint made according to the present invention.

FIG. 1 shows an overall view of wrist splint 10 in an unsecured state. Top panel 18 is intended to lie over the top of the patient's forearm, wrist, and hand. Bottom panel 16 is intended to lie beneath the same anatomy.

The top and bottom panels are preferably shaped to allow at least a portion of the base of the thumb to remain outside the splint. Thus, bottom panel 16 is provided with bottom thumb relief 24 while top panel 18 is provided with top thumb relief 26. The shape of these thumb reliefs may vary according to the treatment modality. If it is desirable to largely immobilize the thumb, then the thumb reliefs will be limited in size. If on the other hand it is desirable to allow the thumb to move, then the thumb reliefs will be larger.

Thumb strap 28 is positioned to pass between the thumb and first finger when the splint is installed. The thumb strap is then suitably secured to the balance of the brace. One way to accomplish this objective is through the use of hook and loop fasteners. In such an embodiment, the exterior of top panel 18 (or at least an appropriate portion thereof) is covered in loop material. Thumb strap 28 is provided with hook tab 31, which is used to secure the thumb strap to the top panel. Tab 30 provides an anchor point for joining hook tab 31 to thumb strap 28. Whenever hook and loop ("VEL-CRO") fastenings are discussed in this application, the reader should understand that the hook panels and loop panel may be reversed as a matter of design choice.

Radius connector 22 and ulna connector 20 are preferably provided to retain the top and bottom panels in the desired orientation when the wrist splint is not installed and during the installation process itself. In the embodiment shown, the radius and ulna connectors are elastic panels. The term "elastic" in this context simply means that the panels are preferably made of a material that will stretch.

FIG. 1B shows an end view of the wrist splint. The reader will observe that the top and bottom panels are separated by a radius gap 56 and an ulna gap 54. Radius connector 22 spans the radius gap while ulna connector 20 spans the ulna gap.

The combination of top panel 18, radius connector 22, bottom panel 16, and ulna connector 20 creates an enclosed central passage 58. This is useful when installing the brace as the patient may simply insert his or her hand through the central passage 58 and pull the wrist splint into the desired position.

One or more stays may be added to the top and/or bottom panels to stiffen them. Two top stay pockets 72 are shown in the illustrated embodiment. A single bottom stay pocket 70 is also shown (more bottom stay pockets could be included). The stay pockets receive stiffening stays (such as aluminum bars) which shape the splint in a desired configuration to properly retain the injured skeletal structures.

It is desirable to provide two or more stay pockets in many embodiments so that at least one of the pockets will lie over the desired portion of the patient's anatomy. A top stay is typically placed over the dorsal mid-line of a patient's wrist. As the orthotic is adjusted to accommodate differing patient wrist diameters, the stay pockets will move relative to this dorsal mid-line. Multiple stay pockets are preferably provided so that the practitioner may relocate the stay to the correct pocket for the particular patient (the pocket which places the stay over the mid-line).

Returning now to FIG. 1, additional features will be described. As discussed previously, the radius gap is spanned by radius connector 22. It is also spanned by radius lace 14, which may be used to selectively adjust the width and shape of the radius gap. Radius tab 12 is connected to the radius lace. It includes features that allow it to be fastened to the rest of the wrist splint. In the embodiment shown, hook panel 52 serves this purpose.

The two ends of the radius lace are attached to top panel 18. The first attachment point is first lace anchor 33. From there the radius lace passes through first eye 40 (in bottom panel 16), second eye 48 (in radius tab 12), third eye 42 (in the bottom panel), fourth eye 34 (in the top panel), fifth eye 36 (in the top panel), sixth eye 44 (in the bottom panel), seventh eye 50 (in the radius tab), eighth eye 46 (in the bottom panel), and then to second lace anchor 38 (in the top panel). The portion of radius lace 14 passing between fourth eye 34 and fifth eye 36 passes beneath the top panel 18 in the embodiment shown.

Using this configuration for radius lace 14 allows the lace to be tightened by pulling on radius tab 12. The operation of the device is dependent to some extent on the type of lace used. The illustrated embodiments use a cord-type lace which has a round cross section and is relatively slick. Grommets or other suitable friction reducing devices are preferably provided for each of the eyes so that the cord-type lace may smoothly pass through the eyes when it is tightened. Other embodiments of the invention may use a band-type lace having a rectangular cross section. A band-type lace produces significantly more friction between the lace and the eyes through which it passes. This phenomenon alters the operation of the invention.

In general, the embodiments using a cord-type lace may be adjusted by the patient using only one hand. The embodiments using a band-type lace must often be adjusted using two hands—requiring assistance by a second person. The cord-type embodiments would therefore seem to be inherently superior. However, there are instances where the band-type lace is preferred, since it allows a practitioner to set a particular desired geometry. The use of both lace types for the adjustment of the orthotic will be described in detail subsequently.

One object of the present invention is to provide a wrist splint which may be adjusted to fit a wide variety of patients. The provision of a radius gap 56 (as shown in FIG. 1B) provides a significant adjustment capacity. This gap may be selectively closed to reduce the circumference of the orthotic—and in fact the edges of the top and bottom panels may be overlapped to produce an even smaller circumference.

The adjustment range provided by the radius gap will be sufficient for many patients and it is therefore appropriate to provide an embodiment which only includes a radius gap. For such an embodiment, top panel 18 and bottom panel 16 could be formed as one integral piece. However, an even greater range of adjustment can be obtained by providing a second gap in the circumference of the orthotic. FIG. 1B shows an embodiment providing a second gap—denoted as ulna gap 54.

FIG. 2 shows the wrist splint from a vantage point where ulna gap 54 may be readily seen. The width of the ulna gap is preferably made variable by an adjustable closure mechanism. The closure mechanism is preferably adjusted and secured using only one hand (so that the patient may operate the mechanism without assistance).

In the version shown in FIG. 2, ulna gap 54 is spanned by ulna lace 62. The two ends of this continuous lace are attached to ulna tab 60. The ulna tab is provided with an attachment feature allowing it to be selectively attached to the balance of the wrist splint. In the embodiment shown, the side of the ulna tab facing away from the user includes a VELCRO hook panel. This engages loop covering 64 on the exterior of the wrist splint. Thus, if the user presses ulna tab 60 against the wrist splint it will become engaged and remain in position.

Figure 3:
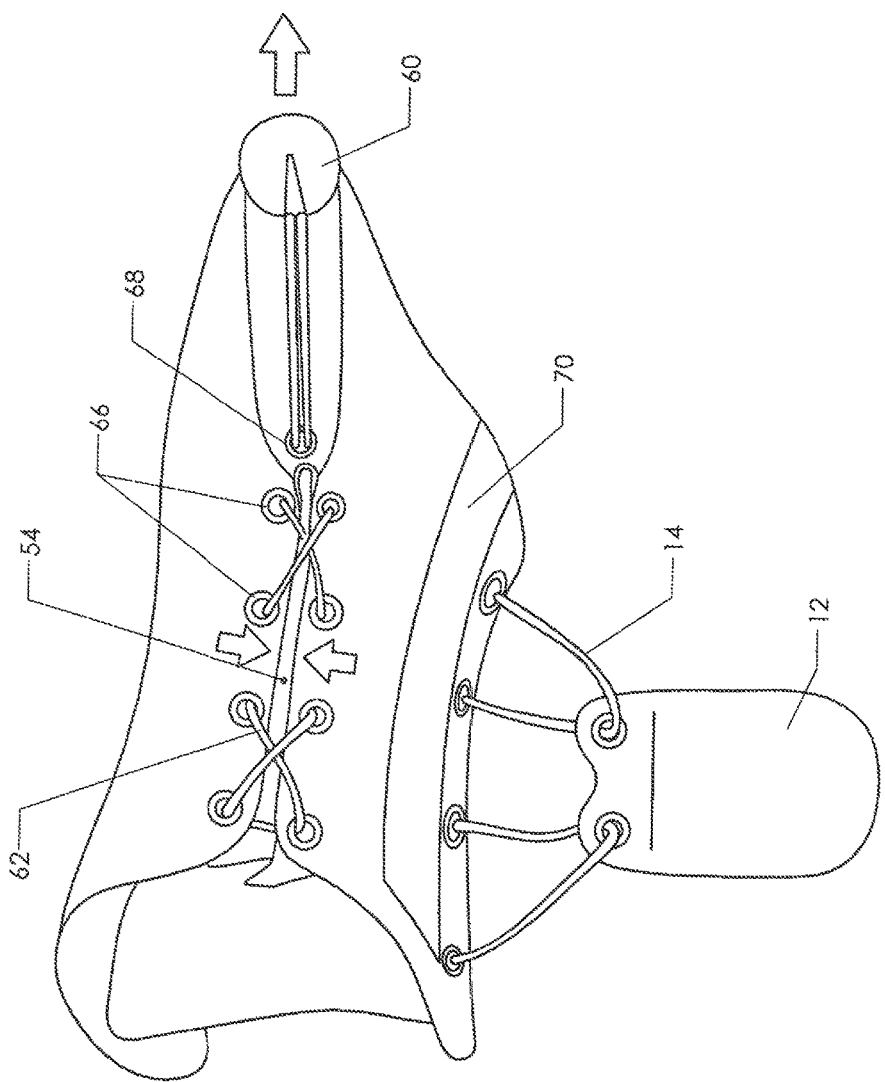
FIG. 3 is a perspective view, showing the closure of the ulna gap.

Ulna lace 62 is threaded through a series of ulna eyes 66 flanking ulna gap 54—in a manner analogous to the lace on a shoe. A cord-type lace is desirable so that friction is minimized. When the user pulls ulna tab 60 to the right in the orientation shown in the view, ulna lace 62 will tighten and draw the top and bottom panels closer together across ulna gap 54 (and may in fact completely close the ulna gap or even cause the edges of the ulna gap to overlap). FIG. 3 shows the view of FIG. 2 after ulna tab 60 has been pulled to the right. The reader will observe the closure of ulna gap 54. Grommets or other suitable friction reducing devices are provided in the ulna eyes and in ulna tab eye 68 to reduce friction as the ulna lace is being tightened.

The configuration shown allows one handed operation so that the user may install the wrist splint and adjust it without assistance. The splint shown is intended for the right wrist. Once the splint is over the wrist, the user may use his or her left thumb and forefinger to grasp ulna tab 60 and pull it to create the desired degree of closure of ulna gap 54. Once this is achieved the user presses the ulna tab against loop covering 64.

Of course, many other adjustable closure mechanisms could be used for the ulna gap. FIG. 11 shows a second embodiment. Adjustment of the ulna gap in this embodiment is provided by a pair of straps 88. Each strap 88 is attached to the orthotic via a strap anchor 90 on a first side of the ulna gap. Two strap rings 86 are attached on the opposite side of the ulna gap by a pair of strap ring anchors 92. The straps are provided with VELCRO hook and loop coverings similar to those used for shoe closures.

In operation, the user grasps a free end of a strap 88 and pulls it tight. He or she then presses the strap back upon itself to secure it in place. The two straps may be adjusted individually to produce a desired configuration.

Figure 4:
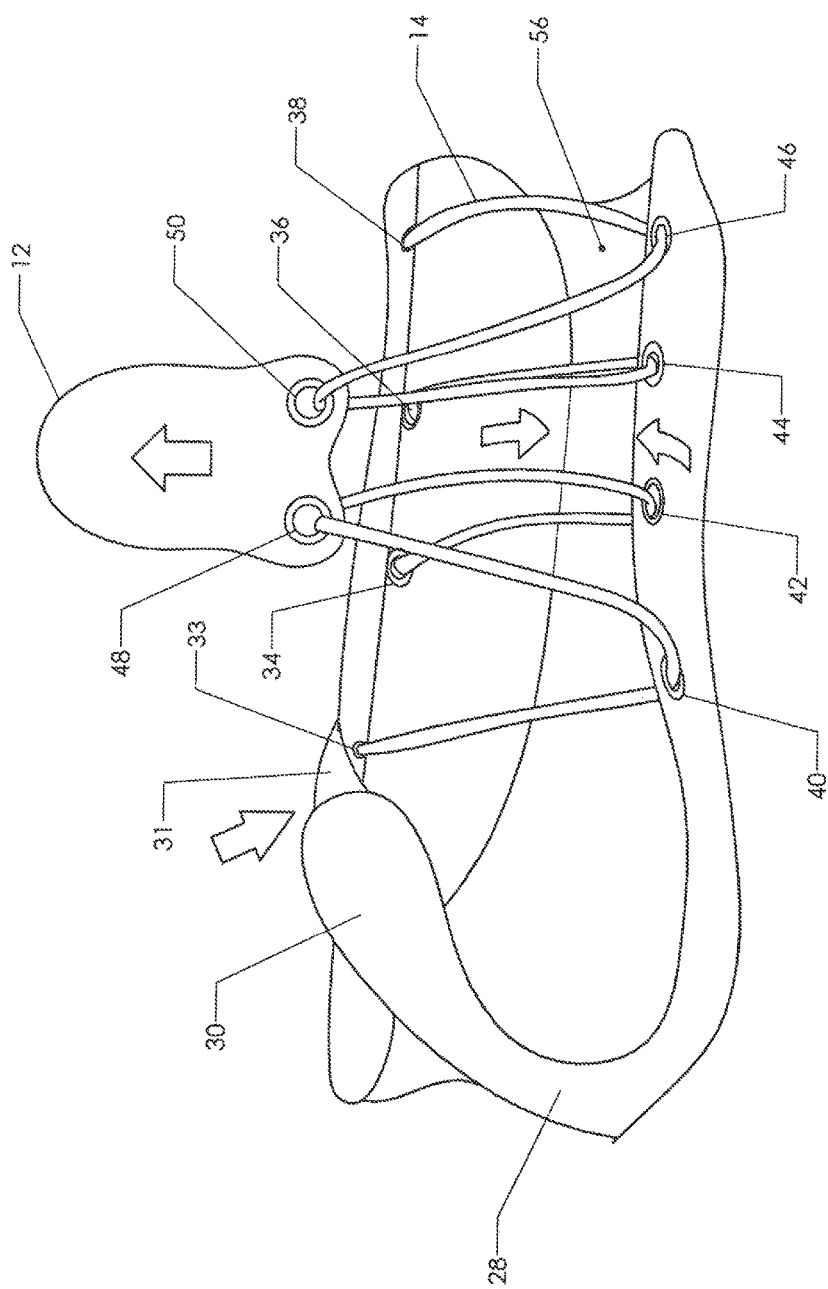
FIG. 4 is a perspective view, showing the closure of the radius gap.

FIGS. 4 through 10 illustrate the configuration of the radius side of the wrist splint during installation of the splint on a patient's wrist and subsequent adjustment. In FIG. 4, hook panel 31 is secured to a suitable position on the exterior of the splint so that tab 30 and thumb strap 28 are properly positioned. The user may then selectively close radius gap 56 by pulling upward on radius tab 12 as indicated.

As mentioned previously, the actual operation of the radius lace assembly is influenced by the type of radius lace used. There are two general types of radius lace which may be used in the device. The first is a cord-type lace. This is a lace having a round cross section and a relatively small diameter. The exterior of a cord-type lace is often provided with a low-friction surface so that it passes easily through the lace eyes.

The second type of lace is a band-type lace which has a flat rectangular cross section. The surface of a band-type lace typically has a higher friction surface. Band-type laces are traditionally used in shoes like canvas basketball sneakers. They allow a lace passing through many eyes to be progressively tightened, since the lace does not easily slip back through an eye even when tension is removed. The operation of the orthotic splint will be described initially using a cord-type lace. The operational differences produced when using a band-type lace will then be explored.

Figure 5:
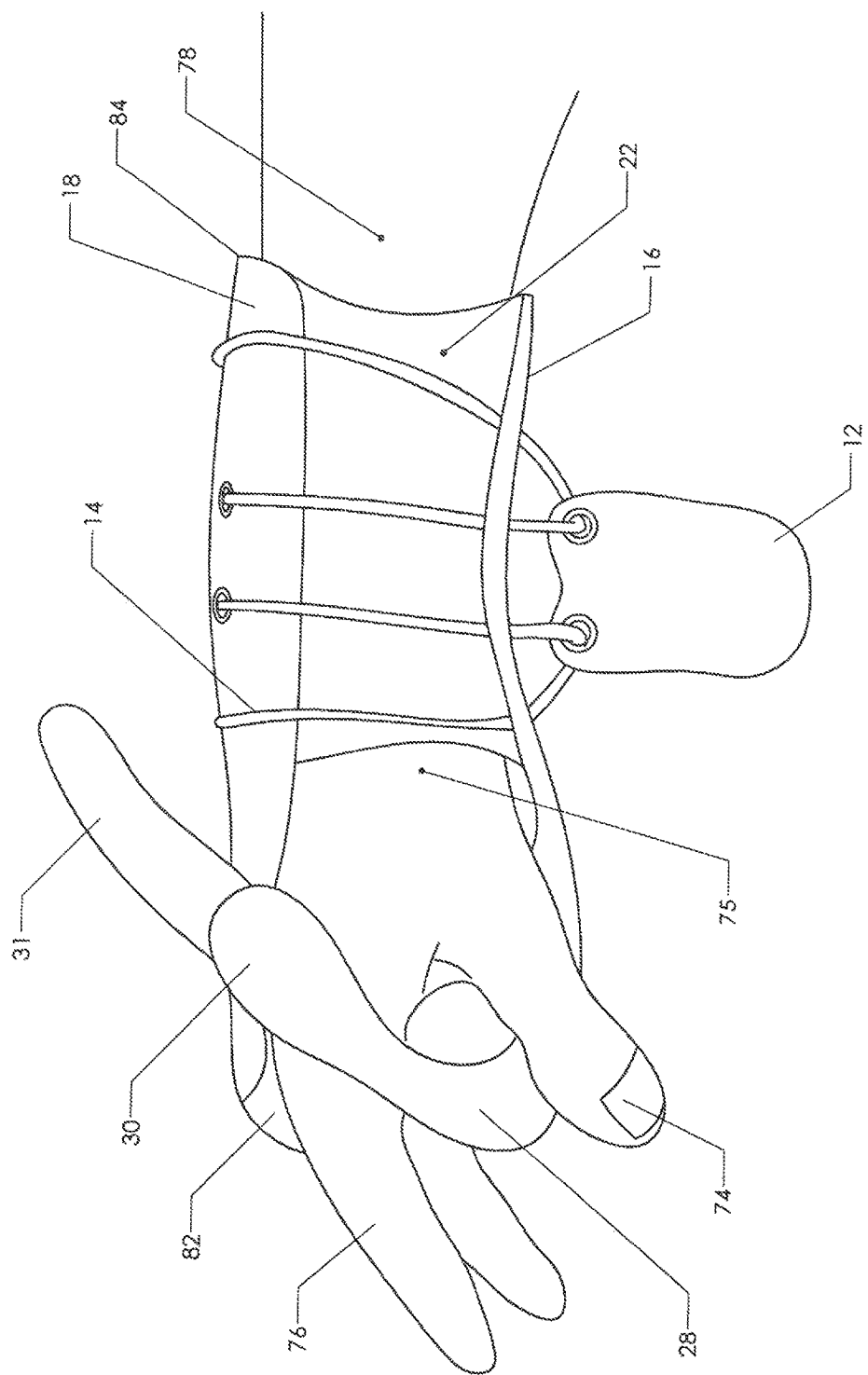
FIG. 5 is a perspective view, showing the wrist splint installed on a patient.

FIGS. 5-10 illustrate the installation of the wrist splint on a patient. In FIG. 5, the splint has been pulled over the patient's wrist 75 into position. Thumb strap 28 is passed between thumb 74 and first finger 76. Hook tab 31 is then pressed against the loop covering on the exterior of top panel 18 to secure the thumb strap in position. The user will next adjust the position of radius tab 12 to selectively close the radius gap around wrist 75.

The top and bottom panels each have a hand end 82 and a forearm end 84. The hand end is closest to the fingers while the forearm end is closest to forearm 78. The position of the radius tab 12 when it is attached to the rest of the orthotic determines the overall width of the radius gap and the taper between the top and bottom panels.

Figure 6:
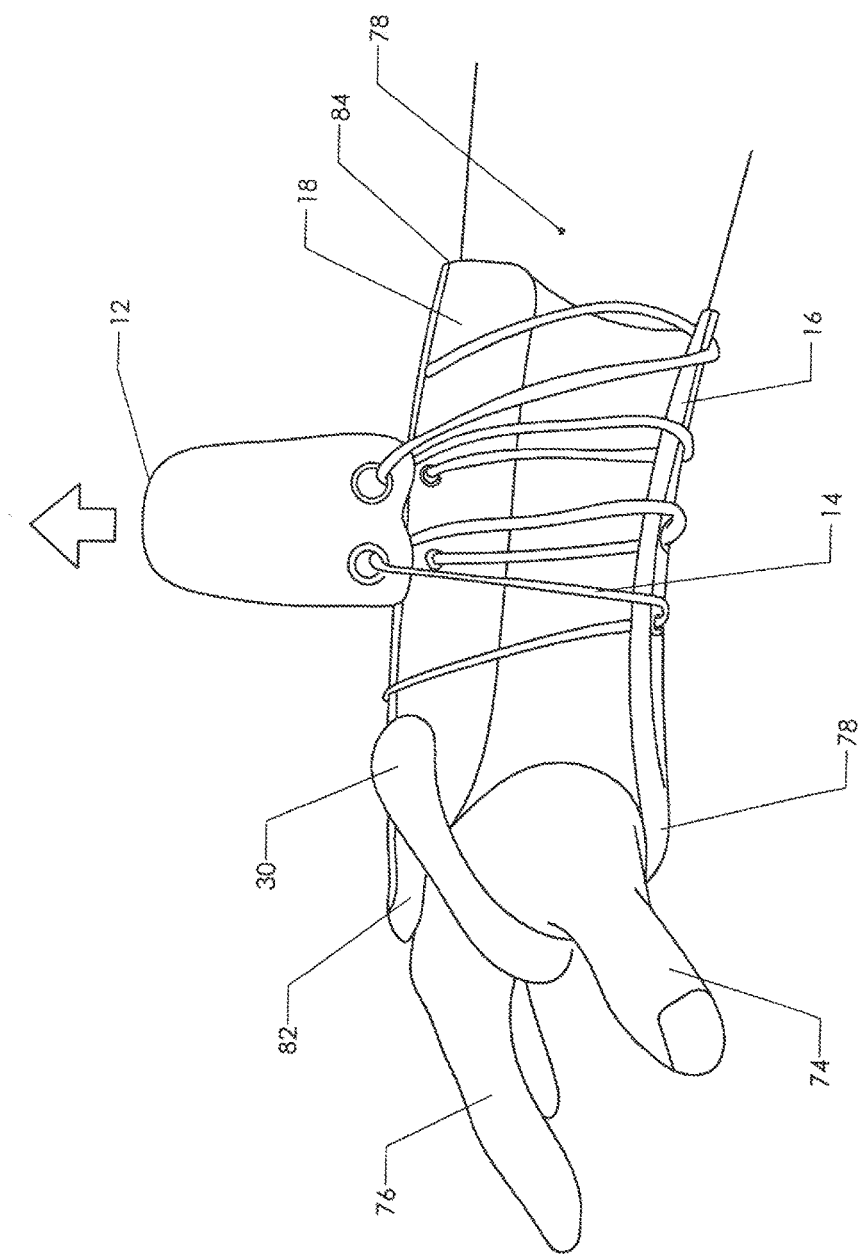
FIG. 6 is a perspective view, showing the use of the radius lace.

When using a cord-type lace, the lace will slide easily through the eyes so that constant tension is maintained even when radius tab 12 is pulled in different directions. If the user pulls straight up on radius tab 12—as indicated in FIG. 6—the top and bottom panels will be drawn evenly together. The lace position and the configuration of the panels are preferably set so that a taper suitable for the average patient is produced by drawing the radius tab straight upward. Thus, a moderate taper will be assumed between the top and bottom panels to accommodate the moderately expanding shape of the forearm in the example of FIG. 6. This will allow the splint to conform to an average individual.

Figure 7:
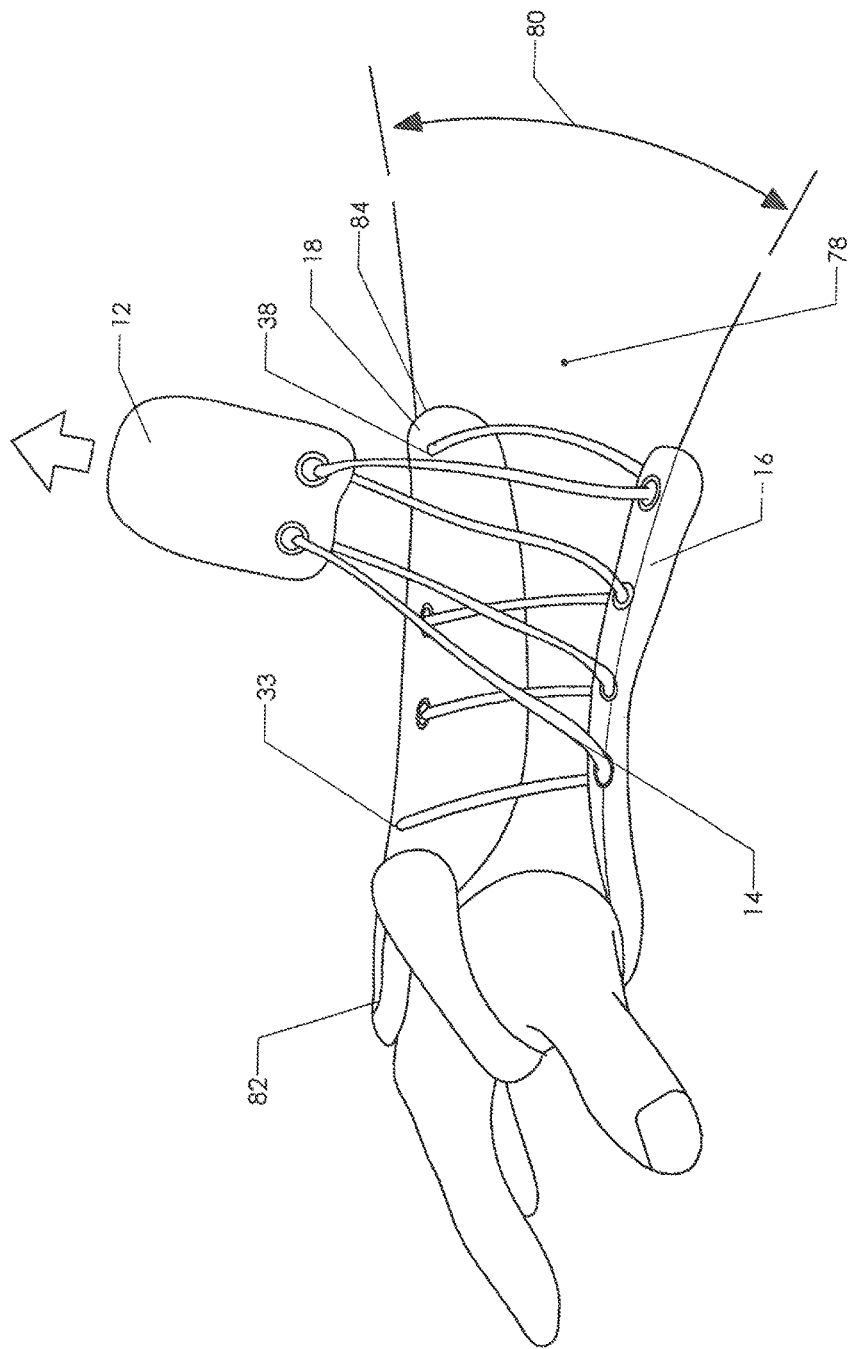
FIG. 7 is a perspective view, showing how pulling the radius tab toward the elbow helps conform the splint to a large forearm.

FIG. 7 shows the application of the wrist splint to a stocky, muscular individual. This individual has a muscular forearm with a wide divergence angle 80. If the wrist splint is tightened conventionally, it will cinch tightly at forearm end 84 while remaining too loose at hand end 82. However, the fact that radius tab 12 may be repositioned allows the user to adjust both the distance between the upper and lower panels and the taper between them.

For the patient shown in FIG. 7, radius tab 12 is pulled toward forearm end 84. Lace 14 passes continuously through the eight eyes on the top panel, the bottom panel, and the radius tab. The use of a cord-type lace allows the lace to pass through the eyes with relatively little friction. Thus, when the radius tab is deliberately pulled toward forearm end 84 as shown, this motion tightens the portions of lace 14 lying proximate hand end 82 before the portions lying proximate forearm end 84 draw tight. The lace tends to "adjust itself" by portions passing through some of the eyes so that tension is evened out.

Figure 9:
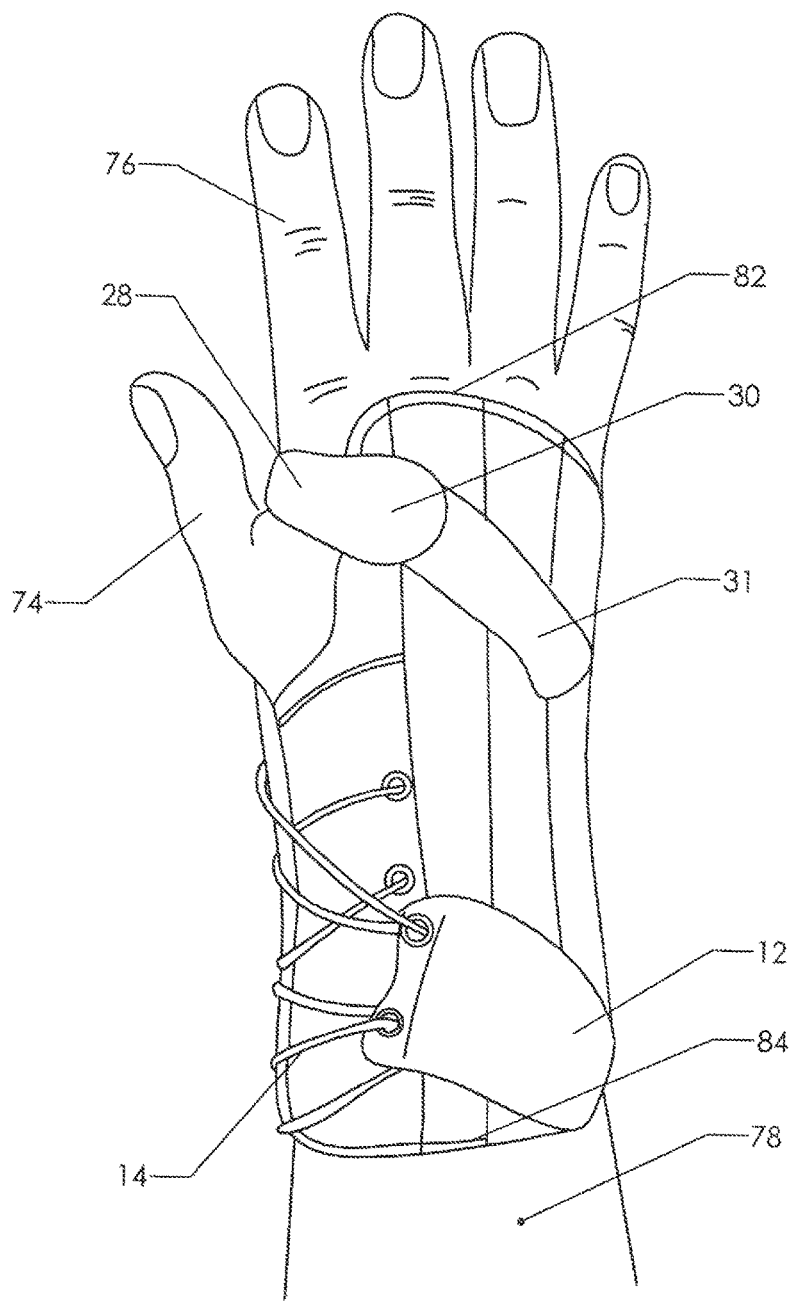
FIG. 9 is a plan view, showing the splint placed on a patient having a large hand and forearm.

Once the radius tab is pulled in this direction and the desired degree of taper is achieved, it is pressed down against the loop material covering the exterior of the wrist splint. The hook panel on the radius tab then holds the radius tab in position. FIG. 9 shows a top view of the wrist splint with the radius tab 12 pressed into position. The wrist splint is thereby appropriately adjusted to accommodate a stocky forearm.

Returning to FIG. 7, the reader will observe that the top and bottom panels are drawn more tightly together in the vicinity of the wrist than in the vicinity of the forearm. This produces a taper in the wrist splint as shown. The top and bottom panels are further apart when moving in the direction of the forearm, which produces a taper consistent with divergence angle 80 of forearm 78.

Figure 8:
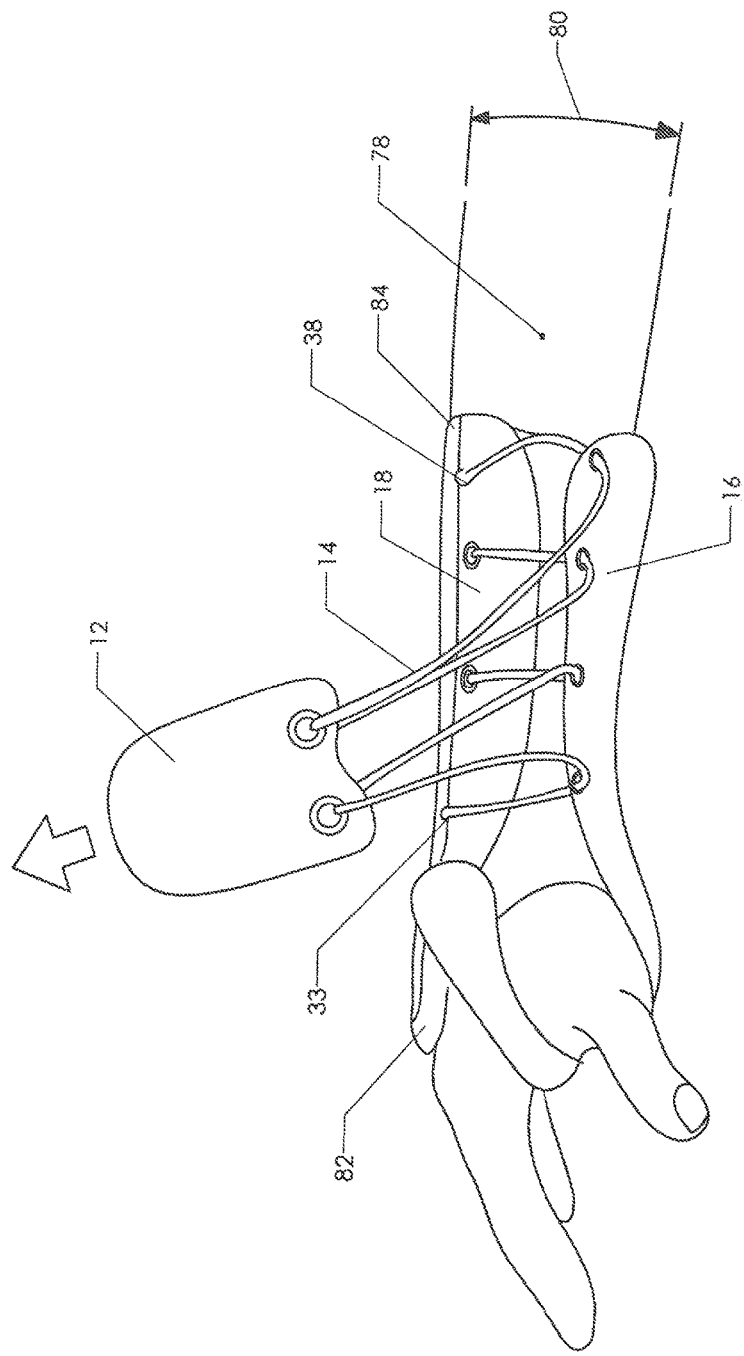
FIG. 8 is a perspective view, showing how pulling the radius tab toward the hand helps conform the splint to a small forearm.

FIG. 8 shows the example of an individual with a slim forearm. If the wrist splint is conventionally tightened for such an individual it will tighten around the wrist while remaining slack near forearm end 84. In order to adjust the orthotic for a patient having a slim forearm, radius tab 12 is pulled toward hand end 82 while it is pulled upward to tighten radius lace 14. This motion causes the portion of radius lace 14 lying proximate forearm end 84 to tighten first, while the portion lying proximate the hand tends to remain slack. The use of a cord-type lace again allows the lace to "adjust itself" in order to create nearly uniform tension. Thus, the top and bottom panels are pulled more tightly together near the forearm. This tends to reduce the "average" taper built into the radius gap and creates a near zero divergence angle 80. Thus, the wrist splint accurately conforms to the slender forearm of the patient shown in FIG. 8.

Figure 10:
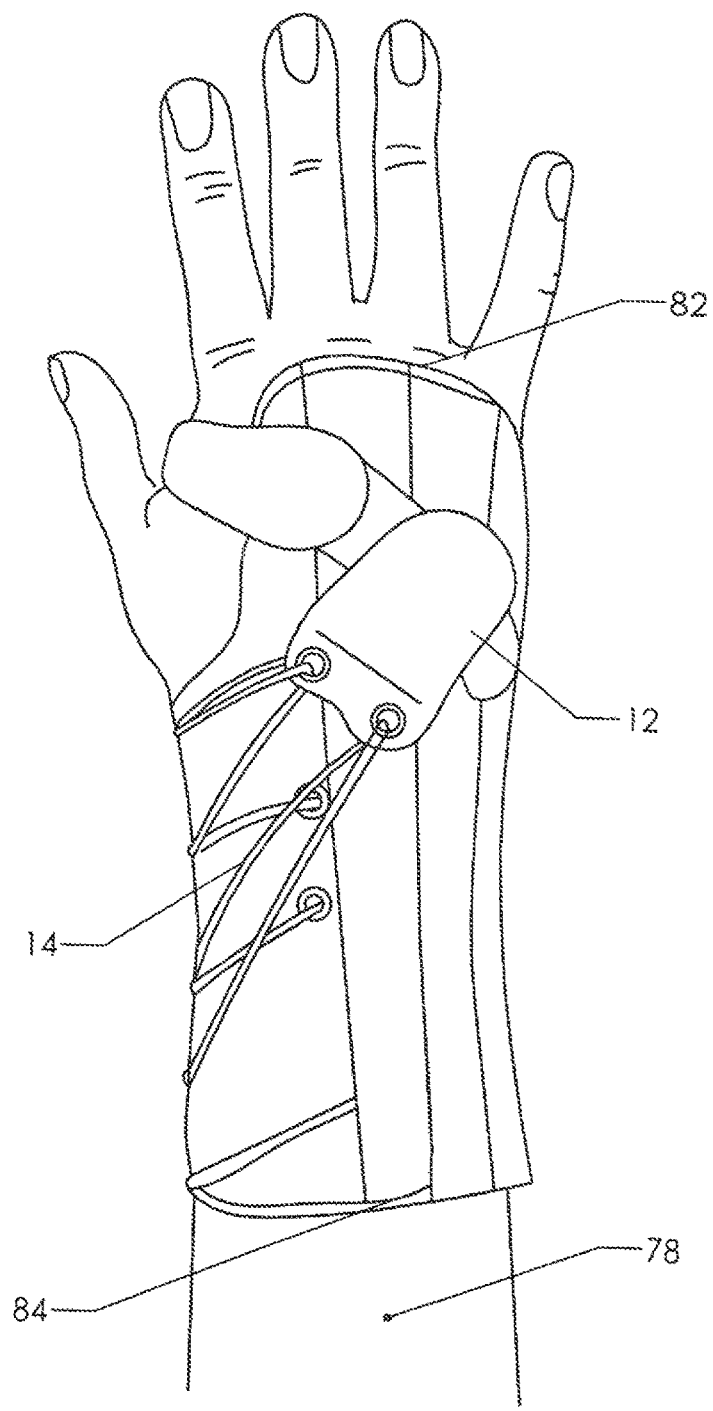
FIG. 10 is a plan view, showing the splint placed on a patient having a small hand and forearm.

The radius tab is then pressed down against the top panel to lock it in position. A top view of this configuration is shown in FIG. 10. The reader will observe how the radius tab is offset in the direction of the hand. The wrist splint is thereby adjusted to conform to the slender forearm geometry of this particular patient.

When using a cord-type lace, the angular offset created by the placement of radius tab 12 must be repeated each time the orthotic is applied. In a sense, the orthotic must be adjusted every time it is applied. A patient will often remove the orthotic to wash, etc. When it is reapplied, radius tab 12 will not be biased toward one position or another (as the relatively low-friction cord-type lace allows it to be easily moved). Thus, the user must properly position radius tab 12 each time.

The use of a band-type lace alters the application process for the orthotic. The band-type lace will not adjust itself by the simple operation of moving the radius tab toward the wrist end or forearm end. Instead, a person must manually pull the lace through the eyes in order to obtain the proper distribution. This step is typically performed by a technician when the orthotic is fitted.

The technician places the splint on the patient and manually applies tension to the portion of the lace protruding between adjacent eyes to obtain the desired taper of the splint (much like manually pulling on the lace of a tall shoe to obtain a desired fit). Once the desired lace arrangement is obtained, radius tab 12 will naturally be offset toward the hand end or the forearm end (It will move toward the correct position when the user pulls on it to draw the lace tight). The user then presses radius tab 12 against the orthotic to secure it in position.

When the orthotic using a band-type lace is removed, lace 14 must be slackened sufficiently to allow the patient's hand to be pulled free. However, the offset of radius tab 12 will tend to remain intact. When the orthotic is next placed on the wrist, the patient can simply pull on the radius tab (without having to pay too much attention to where it should be placed) and the radius tab will tend to return to the position originally set by the technician. Thus, the use of a band-type lace allows the orthotic to be adjusted initially by a technician and retain the configuration set by the technician. The use of a cord-type lace requires that the configuration be set each time the device is applied.

The selection of one type of lace over the other is a question of individual preference. The offset of radius tab 12 (whether set by a technician or the patient) retains the desired taper between top panel 18 and bottom panel 16.

Having thus received a description of a preferred embodiment of the invention, those skilled in the art will immediately recognize that many more alternate embodiments are possible. As an example, the radius tab is attached to the orthotic by hook and loop fasteners in the preferred embodiment described. An array of plastic snap closures could be substituted for this approach. In another embodiment, the ulna gap could be eliminated altogether with the top and bottom panels being formed as one continuous piece broken only by the radius gap.

Although the preceding description contains significant detail, it should not be viewed as limiting the invention but instead as providing illustrations of the preferred embodiments of the invention. Many other alterations could be made to the embodiments illustrated without altering the substance of the invention. Thus, the scope of the present invention should be defined by the following claims rather than any specific examples given.

The invention claimed is:

1. A method for attaching a wrist splint to a patient having a hand, a wrist, a thumb, a first finger, and a forearm, comprising:
   a. providing a wrist splint, including
      i. a top panel,
      ii. a bottom panel
      iii. a radius gap between said top panel and said bottom panel, located on a first side of said wrist splint,
      iv. a first adjustable closure mechanism configured to adjustably close said radius gap,
      v. an ulna gap between said top panel and said bottom panel, located on a second side of said wrist splint, with said second side being opposite said first side, said ulna gap being bounded by a first edge on said top panel and a second edge on said bottom panel;
      vi. a second adjustable closure mechanism configured to adjustably close said ulna gap, said second adjustable closure mechanism including an ulna tab configured to close said ulna gap when moved in a direction that is parallel to said first edge on said top panel,
      vii. a thumb strap selectively connecting said top panel to said bottom panel;
   b. installing said wrist splint on said hand, wrist, and forearm of said patient by placing said wrist splint around said hand, wrist, and forearm and passing said thumb strap around said hand between said thumb and said first finger;
   c. adjusting said first adjustable closure mechanism in order to close said radius gap to a desired degree; and
   d. adjusting said second adjustable closure mechanism in order to close said ulna gap to a desired degree.

2. The method for attaching a wrist splint as recited in claim 1, wherein said second adjustable closure mechanism comprises:
   a. a plurality of ulna eyes along said first edge and said second edge bounding a said ulna gap;
   b. an ulna lace threaded through said plurality of ulna eyes and spanning said ulna gap;
   c. said wrist splint including an ulna tab eye proximate said ulna gap;
   d. said ulna lace including a first end and a second end, with said first end and said second end being threaded through said ulna eyes;
   e. an ulna tab connected to said first and second ends of said ulna lace, said ulna tab having a hook and loop panel facing said wrist splint; and
   f. a hook and loop panel on said wrist splint facing said ulna tab, said hook and loop panel lying parallel to said ulna gap.

3. The method of attaching a wrist splint as recited in claim 2, wherein said ulna tab is made large enough to be grasped between a thumb and a forefinger.

4. The method of attaching a wrist splint as recited in claim 2, wherein said ulna tab is made large enough to be grasped between a thumb and a forefinger.

5. The method for attaching a wrist splint as recited in claim 1,
wherein said wrist splint includes an ulna connector connecting said top panel to said bottom panel across said ulna gap.

6. The method of attaching a wrist splint as recited in claim 5, wherein said ulna connector is an elastic panel.

7. The method of attaching a wrist splint as recited in claim 5, wherein said thumb strap is attached to said top panel by a hook and loop fastener.

8. The method of attaching a wrist splint as recited in claim 1, wherein said thumb strap is attached to said top panel by a hook and loop fastener.

9. A method for attaching a wrist splint to a patient having a hand, a wrist, a thumb, a first finger, and a forearm, comprising:
   a. providing a wrist splint, including
      i. a top panel,
      ii. a bottom panel,
      iii. an ulna gap positioned to lie proximate an ulna bone in said patient's forearm,
      iv. said ulna gap lying between said top panel and said bottom panel, with said ulna gap being bounded by a first edge on said top panel and a second edge on said bottom panel,
      v. providing an ulna lace spanning said ulna gap,
      vi. providing an ulna tab connected to said ulna lace,
      vii. providing an adjustable attachment between said ulna tab and said wrist splint, wherein said ulna tab and said ulna lace are configured to close said ulna gap when said ulna tab is moved in a direction that is parallel to said first edge on said top panel,
   b. installing said wrist splint on said hand, wrist, and forearm of said patient;
   c. pulling said ulna tab in order to tighten said ulna lace and thereby close said ulna gap to a desired degree; and
   d. attaching said adjustable attachment between said ulna tab and said wrist splint in order to maintain said ulna tab in position.

10. The method for attaching a wrist splint as recited in claim 9, wherein:
   a. said wrist splint includes a plurality of ulna eyes along said first edge and said second edge bounding said ulna gap;
   b. said wrist splint includes an ulna tab eye;
   c. said ulna lace passes through said plurality of ulna eyes and said ulna tab eye; and
   d. said ulna lace includes a first end and a second end, wherein said first and second ends of said ulna lace are attached to said ulna tab.

11. The method of attaching a wrist splint as recited in claim 10, wherein said ulna tab is made large enough to be grasped between a thumb and a forefinger.

12. The method for attaching a wrist splint as recited in claim 9, wherein:
   a. said wrist splint includes a thumb strap connecting said top panel to said bottom panel.

13. The method for attaching a wrist splint as recited in claim 12, wherein said wrist splint includes an ulna connector connecting said top panel to said bottom panel across said ulna gap.

14. The method of attaching a wrist splint as recited in claim 13, wherein said ulna connector is an elastic panel.

15. The method of attaching a wrist splint as recited in claim 13, wherein said thumb strap is attached to said top panel by a hook and loop fastener.

16. The method of attaching a wrist splint as recited in claim 12, wherein said thumb strap is attached to said top panel by a hook and loop fastener.

17. The method of attaching a wrist splint as recited in claim 12, wherein said ulna tab is made large enough to be grasped between a thumb and a forefinger.

18. The method of attaching a wrist splint as recited in claim 9, wherein said ulna tab is made large enough to be grasped between a thumb and a forefinger.

* * * * *